United States Patent [19]

Kusuhara

[11] Patent Number: 4,641,227

[45] Date of Patent: Feb. 3, 1987

[54] SOLAR SIMULATOR

[75] Inventor: Masaki Kusuhara, Tokyo, Japan

[73] Assignee: Wacom Co., Ltd., Japan

[21] Appl. No.: 766,124

[22] Filed: Aug. 15, 1985

[30] Foreign Application Priority Data

Nov. 29, 1984 [JP] Japan .................................. 59-252698
May 24, 1985 [JP] Japan .................................. 60-110542

[51] Int. Cl.⁴ .............................................. F21V 9/00
[52] U.S. Cl. .................................... 362/231; 362/232; 362/293
[58] Field of Search ................ 362/231, 263, 293, 232

[56] References Cited

U.S. PATENT DOCUMENTS 4,488,207 12/1984 Harmon ............................. 362/231

Primary Examiner—Carroll B. Dority, Jr.
Attorney, Agent, or Firm—Kinney & Lange

[57] ABSTRACT

A solar simulator produces synthetic spectral distribution characteristic with sufficiently high uniformity and repeatability and permits the intensity of output light to be varied without substantially deviating the spectral distribution of output light. The solar simulator includes filter means capable of eliminating the near infrared component from the light of a xenon short arc lamp and, extracting the near infrared component from the light of an incandescent filament lamp enable the two kinds of lights which are selected by the filter means to be directed coaxially to an integrating optical system.

15 Claims, 14 Drawing Figures

SOLAR SIMULATOR

BACKGROUND OF THE INVENTION (1) Field of the Invention

This invention relates to a solar simulator, and more particularly to a solar simulator which enjoys simplicity of construction and approximation to the spectral (energy) distribution of natural sunlight and permits optical intensity to be varied without affecting spectral (energy) distribution.

(2) Description of the Prior Art

The solar simulator, as well known, is a light-source device for reproducing the spectral distribution of natural sunlight with high accuracy. This solar simulator is indispensable to determination of performances of various devices using solar energy, such as the photoelectric conversion property of a solar cell, and to accelerated degradation test of such performances.

In the conventional solar simulators, xenon short arc lamps have been popularly used. Incidentally, the light from the xenon short arc lamp has a group of sharp and complicate peaks in the near infrared region (800 to 1,000 nm) as illustrated in the spectral distribution diagram of FIG. 1. Frequently, therefore, the xenon short arc lamp is used in combination with a multilayer interference filter adapted to compensate these peaks evenly and approximate the spectral distribution of this light to that of natural sunlight.

A typical spectral distribution of the light emitted from the solar simulator using the xenon short arc lamp so compensated as described above is indicated by the solid line in FIG. 2. The chain line found in the diagram indicates the spectral distribution of natural sunlight (under the condition of air mass zero).

As noted also from FIG. 2, in the conventional solar simulator, the spectral distribution thereof is fairly close on the average to that of natural sunlight and the conventional solar simulator can be put to practical use.

For more accurate measurement of the photoelectric conversion property exhibited under natural sunlight by the solar cell of varying grade possessed of spectral sensitivity characteristics over a wide range from ultraviolet region through near infrared region as illustrated in FIG. 3, the conventional solar simulator which resorts to the combination of a xenon lamp and a multilayer interference filter or, generally a dichroic filter is still insufficient.

This is because a small group of peaks remain in the near infrared region (in the range of 750 nm) to 1,000 nm as noted from the spectral distribution diagram of FIG. 2 and these peaks cause an error in the measurement.

As means of diminishing the aforementioned group of peaks thereby approximating the spectral distribution to that of natural sunlight and enhancing the spectral accuracy, it has been proposed to combine the light emitted by the xenon short arc lamp having a relatively continuous spectral distribution in the ultraviolet region through the visible region and the light emitted by the incandescent filament (tungsten halogen) lamp having a continuous spectral distribution in the near infrared region in an overlapped or mixed state.

A typical synthetic spectral distribution obtained by the combination is illustrated in FIG. 4.

In the diagram, the curve L1 represents the spectral distribution characteristic of the light emitted by the xenon short arc lamp minus the component falling on the longer wavelength side than the near infrared and the curve L2 the spectral distribution characteristic of the light emitted by the incandescent filament lamp minus the components of visible light and ultraviolet light.

The curve L3 represents the synthetic spectral distribution characteristic obtained by having the aforementioned curves L1 and L2 combined in an overlapped or mixed state. The curve L4 of solid line representing the same spectral distribution characteristic of natural sunlight as shown in FIG. 2 for the purpose of comparison.

It is seen from FIG. 4 that a spectral distribution (curve L3) satisfactorily approximating the spectral distribution (curve L4) of natural sunlight is obtained and the group of irregular peaks in the near infrared region which has been responsible for the erroneous measurement obtained by the conventional solar simulator can be diminished by combining the light emitted by the xenon short arc lamp minus the component on the longer wavelength side than the near infrared light (curve L1) and the light emitted by the incandescent filament lamp minus the components of visible light and ultraviolet light (curve L2) in an overlapped or mixed state.

In a generally conceivable specific configuration of the solar simulator possessing such a spectral distribution as described above, a first light-source device combining a xenon short arc lamp and a filter capable of eliminating the light on the longer wavelength side than the near infrared light and a second light-source device combining an incandescent filament lamp and a filter capable of eliminating the light in the visible and ultraviolet regions are prepared and disposed in such a manner that the beams of light emitted from these two light-source devices will be directed to a single integrating optical system to be combined in an overlapped or mixed state.

It is suspected, however, that this configuration entails the following drawbacks.

(1) Since the configuration necessitates use of the same number of filters (such as dichroic filters) as the total number of xenon short arc lamps and incandescent filament lamps, the apparatus used therefor is large and the maintenance of this apparatus is complicated and the cost of the apparatus is high.

(2) It is extremely difficult for the plurality of filters to be produced with mutually equal filter properties. Thus, the synthetic spectral distribution characteristic obtainable by the present configuration is deficient in uniformity and repeatability.

(3) To heighten the focusing efficiency, the apparatus necessitates use of large focusing mirrors or lenses and large filters. As a multilayer interference filter gains in size, it becomes extremely difficult to equalize filter characteristic in the central part and the peripheral part of the filter. Thus, the apparatus obtains as high synthetic spectral distribution as designed only with extreme difficulty.

SUMMARY OF THE INVENTION

An object of this invention is to provide a solar simulator which produces synthetic spectral distribution characteristic with sufficiently high uniformity and repeatability and which is relatively small and inexpensive.

Another object of this invention is to provide a solar simulator which permits the intensity of output light to be varied without substantially deviating the spectral distribution of synthetic output light from that of natural sunlight.

This invention is characterized by being constructed so as to incorporate in the solar simulator single filter means capable of eliminating the near infrared component from the spectrum of the light of a xenon short arc lamp and, at the same time, extracting the near infrared component from the spectrum of the light of an incandescent filament lamp and enable the said near infrared component light emitted by the incandescent filament lamp and the light emitted by the xenon short arc lamp minus the near infrared component to be directed coaxially to a single integrating optical system.

In the solar simulator constructed as described above, this invention is further characterized by enabling the intensity of the light on a sample plane to be adjusted by moving an incandescent filament lamp toward or away from the sample plane in the direction of optical axis and by controlling the electric current supplied to the xenon short arc lamp and allowing both of the position of the incandescent filament lamp and the magnitude of the electric current supplied to the xenon short arc lamp to be synchronously controlled thereby causing the intensity of the light from one of the light sources on the sample plane to be proportionally varied when the intensity of the light from the other light source on the sample plane is varied and keeping the difference or ratio between the intensities of the lights from the two light sources to be equal to a value fixed in advance in conformity with the intensity of light on the sample plane.

DETAILED DESCRIPTION OF THE PREFERRED EMBODIMENTS

Figure 5:
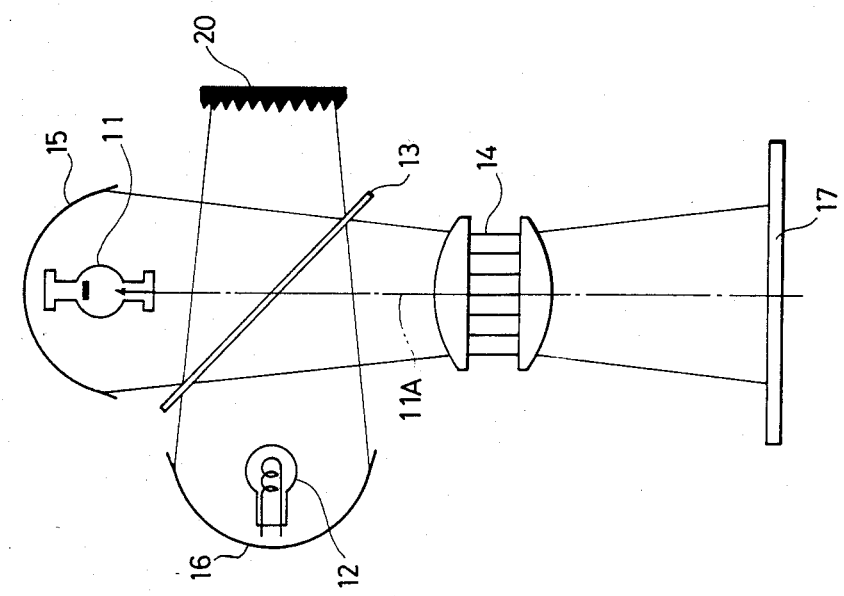
FIG. 5 and FIG. 6 are schematic side views of solar simulators as embodiments of the present invention.

Now, the first embodiment of this invention will be described in detail below with reference to the accompanying drawings. In FIG. 5, a xenon short arc lamp 11 has a focusing mirror 15 and an integrating optical system 14 is disposed on the optical axis 11A of the xenon short arc lamp 11.

Between the xenon short arc lamp 11 and the integrating optical system 14, a cold filter 13 is disposed in such a posture as to intersect the aforementioned optical axis 11A (desirably at an angle of 45°). The aforementioned cold filter 13 serves to reflect infrared light and permit passage of visible light and ultraviolet light.

An incandescent filament lamp 12 has a focusing mirror 16. The light emitted from the incandescent filament lamp 12 is projected on the integrating optical system 14 side of the cold filter 13. The near infrared component of the incident light reflected on the cold filter 13 is collimated in the direction of the integrating optical system 14 coaxially with the visible and ultraviolet components of light issued from the xenon short arc lamp 11, reflected by the focusing mirror 15, and passed through the cold filter 13.

The light combined in an overlapped or mixed state by the cold filter 13 and the integrating optical system 14 is evenly dispersed on a sample plane 17. A heat collector 20 serves to absorb the infrared and near infrared components of light from the xenon short arc lamp reflected by the cold filter 13.

It is evident that the embodiment of FIG. 5 permits simplification and compaction of construction and reduction of cost because the elimination of the infrared and near infrared components of the light emitted by the xenon short arc lamp 11 and the extraction of the near infrared component of the light emitted by the incandescent filament lamp 12 are both accomplished by the single cold filter 13.

This embodiment has the advantage that since the extraction of the longer wavelength component and the shorter wavelength component from the lights of the two light sources and the addition of said two components are effected by one filter (cold filter), the spectral distribution of the final output light is not appreciably varied even when the filter property of the cold filter 13 is more or less varied.

Consequently, the tolerance for the filter property of the cold filter 13 is widened and the production cost of the cold filter 13 is proportionately lowered.

Figure 6:
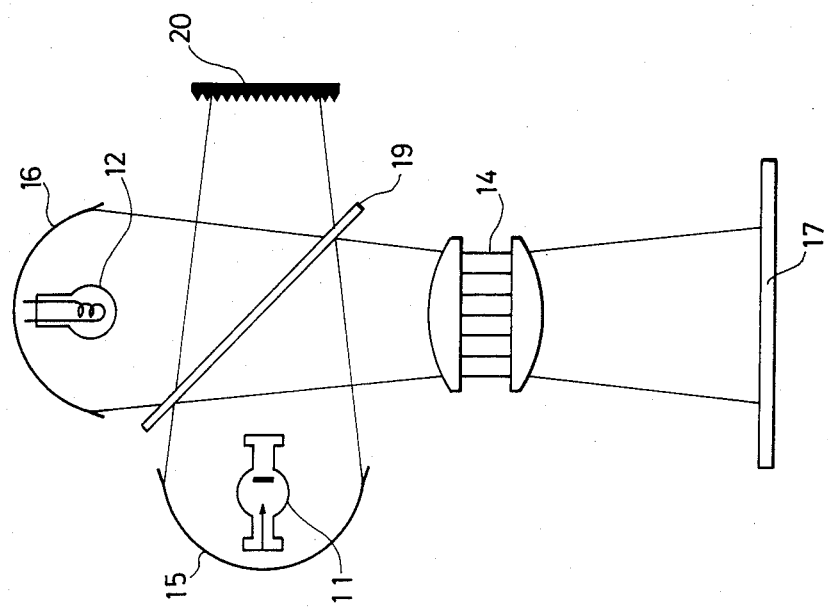

FIG. 6 is a side view illustrating in outline the construction of another embodiment of this invention. In this diagram, the same numerical symbols as found in FIG. 5 denote identical or equivalent components.

As easily noted from the comparison of FIG. 6 with FIG. 5, the second embodiment equals the first embodiment illustrated in FIG. 5, except that the xenon short arc lamp 11 and the incandescent filament lamp 12 have change places with each other and with a heat transmitting cold mirror 19 is substituted for the cold filter 13. The heat transmitting cold mirror 19 serves to permit passage of infrared light and reflect visible light and ultraviolet light.

Evidently, the construction of FIG. 6 brings about entirely the same operation and effect as the embodiment of FIG. 5.

In either of the embodiments described above, the synthetic spectral distribution characteristic of the output light obtained on the sample plane 17 can be approximated more to the spectral distribution of natural sunlight by using, in place of the focusing mirror 16, a multilayer interference filter adapted to permit passage of part of the infrared light and consequently effect compensation of the spectral distribution of the infrared region and suitably selecting the spectral reflectance characteristic of the focusing mirror 15.

Figure 7:
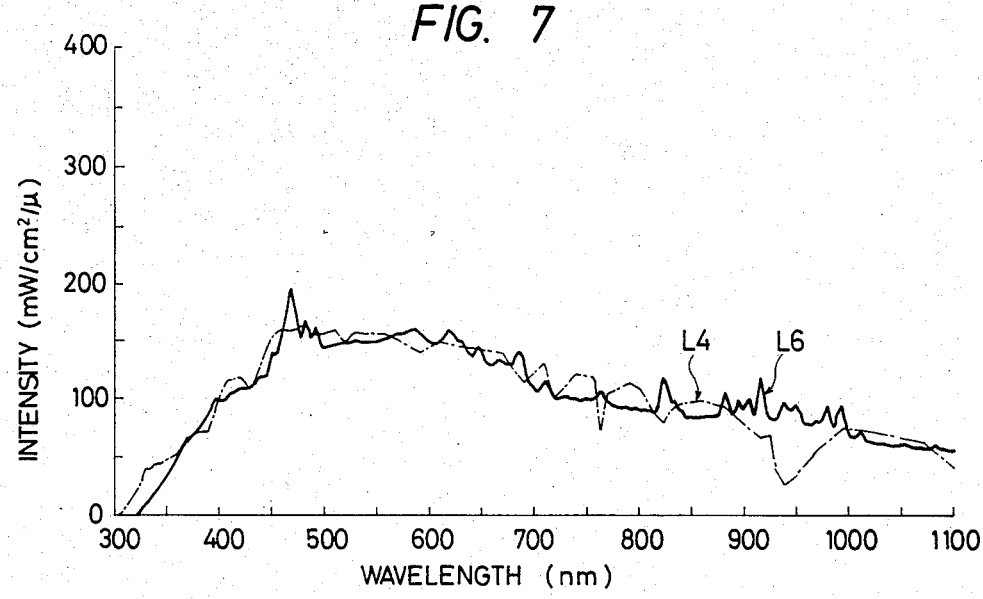
FIG. 7 is a diagram illustrating the spectral distribution obtained by the solar simulators of FIG. 5 and FIG. 6.

Even in that case, it has been experimentally demonstrated by the inventors that the solar simulator shown in FIG. 6 so modified exhibits a fairly higher spectral intensity as shown by the curve L6 in the spectral distribution diagram of FIG. 7 than the spectral intensity of natural sunlight (curve L4 in FIG. 7) in the wavelength region of about 950 nm.

Figure 3:
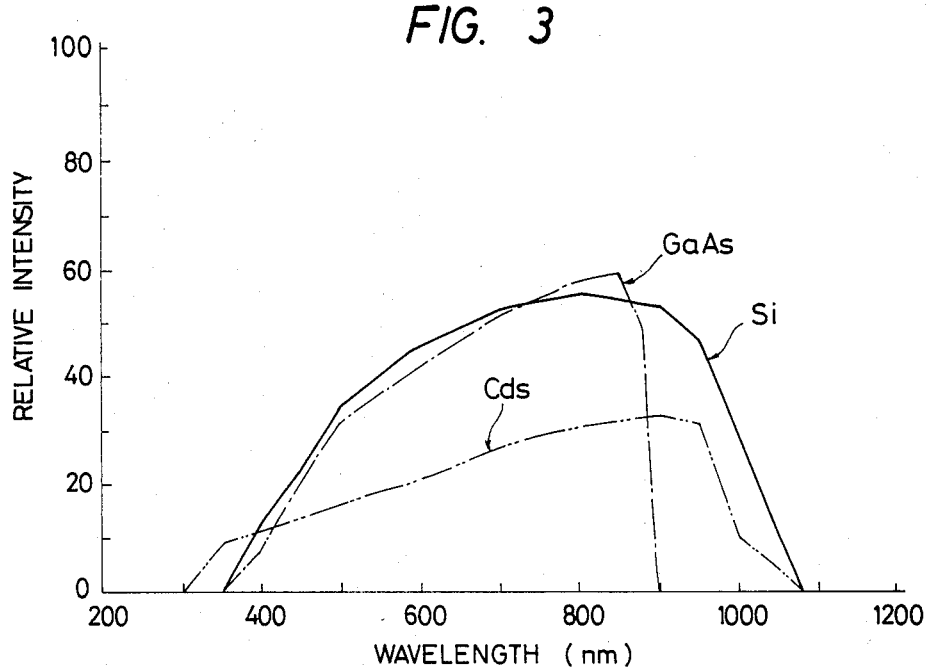
FIG. 3 is a diagram illustrating the spectral sensitivity characteristic of various solar cells.

It is noted from FIG. 3 that Si and CdS exhibit high sensitivity to the light in the neighbourhood of 950 nm, therefore, there ensues the problem that in the test involving such substances the approximation to natural sunlight is not obtained sufficiently.

Figure 8:
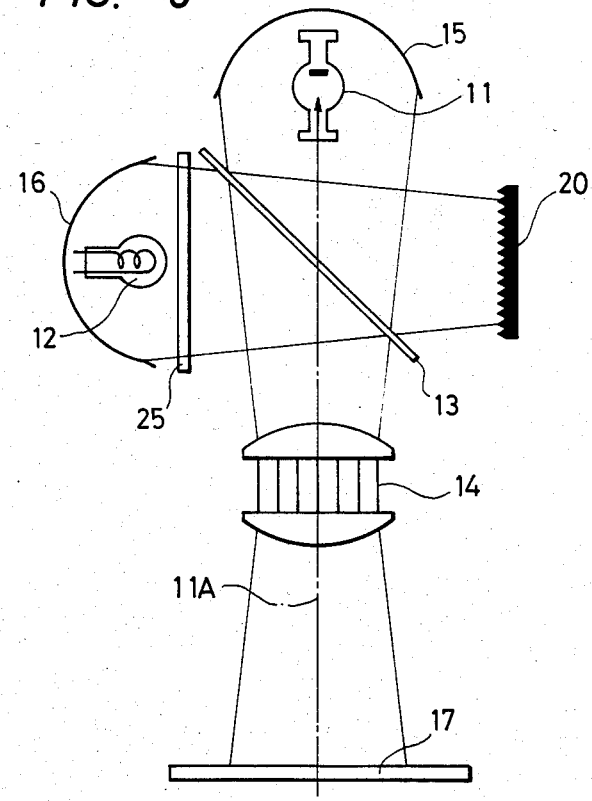
FIG. 8 is a schematic side view illustrating a third embodiment of the present invention.

The third embodiment of this invention aimed at solving this problem is illustrated in FIG. 8.

As noted from the comparison of FIG. 8 with FIG. 5, this embodiment equals the embodiment of FIG. 5, except that a water filter 25 is disposed between the incandescent filament lamp 12 and the heat reflecting cold filter 13 so as to preclude the interception of the light from the xenon short arc lamp 11.

Figure 9:
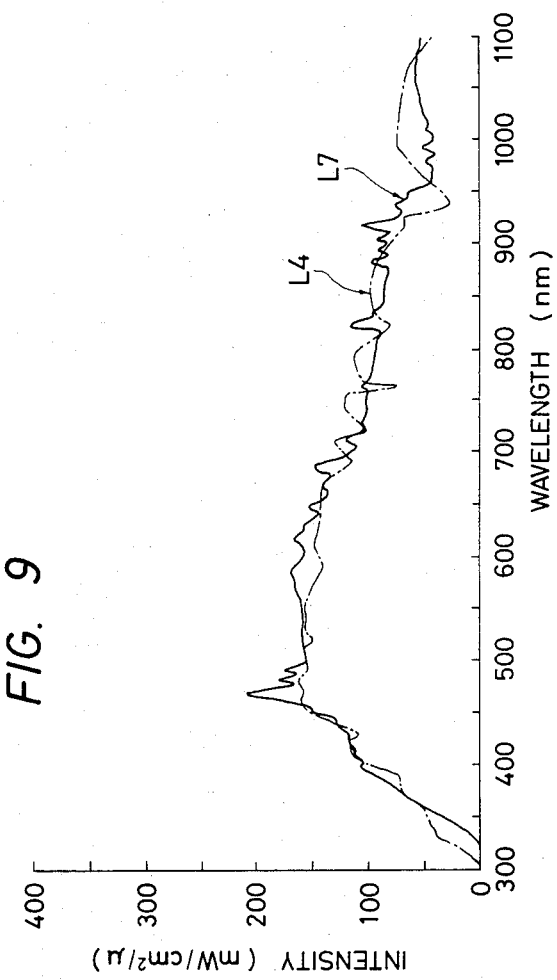
FIG. 9 is a diagram illustrating the spectral distribution obtained by the embodiment of FIG. 8.

Since the water filter 25 possesses a property of selectively absorbing the light in the neighborhood of 950 nm, the spectral distribution of simulated solar light obtained by the third embodiment of this invention, as indicated by the curve L7 in the spectral distribution of FIG. 9, is sufficiently approximated to that of natural sunlight (curve L4 of FIG. 9).

Figure 10:
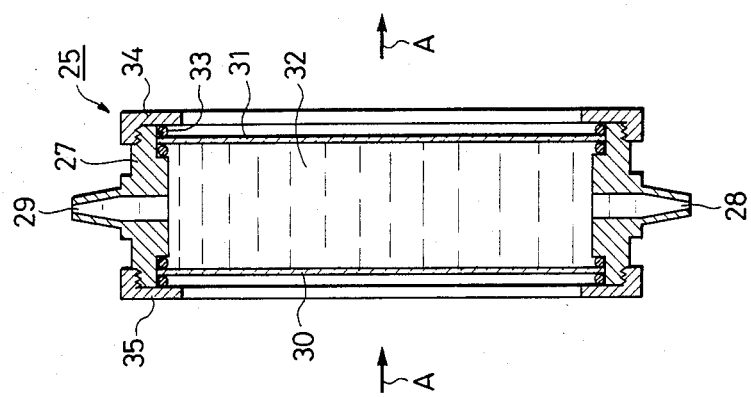
FIG. 10 is a schematic cross section illustrating a typical water filter to be used in the embodiment of FIG. 8.

FIG. 10 is a cross section illustrating a typical construction of the water filter 25 suitable for use in the third embodiment. A hollow tubular body 27 is provided with a water inlet 28 and a water outlet 29 which are disposed desirably as diametrically opposed to each other. To the end faces of the hollow tubular body 27, transparent sheets (made of glass or quartz glass) 30, 31 are attached watertightly. The cavity in the filter body is filled with water 32.

In FIG. 10, 33 denotes an O ring, 34, 35 denote clamp nuts for fitting the aforementioned transparent sheets 30, 31 watertightly to the tubular body 27, and the arrows A, A denote the path for light.

As readily inferred by any person of ordinary skill in the art, the amount (or ratio) of absorption of the light in the neighborhood of 950 nm can be adjusted by changing the thickness of water layer in the direction of the aforementioned light path A—A. Although the thickness of the aforementioned water layer can be freely fixed as desired, it has been demonstrated by the inventors' experiment that satisfactory results of the water filter are obtained when this thickness is in the range of 5 mm to 25 mm.

Even when the aforementioned water filter 25 is disposed in the path for the light obtained in consequence of the combination of the light from the incandescent filament lamp 12 and the light from the xenon short arc lamp 11 in a mixed state, i.e. between the heat reflecting cold filter 13 and the surface of the sample plane 17, it brings about the same effect as when it is disposed at the position indicated in FIG. 8.

Evidently, the same water filter can be applied to the second embodiment illustrated in FIG. 6.

Figure 11:
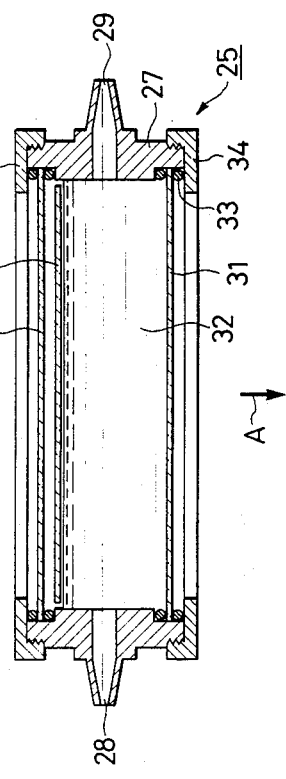
FIG. 11 is a schematic cross section illustrating another typical water filter to be used in the embodiment of FIG. 8.

Optionally, the surfaces of the water filter which are perpendicular to the light path A—A may be disposed in a horizontal direction as illustrated in FIG. 11 instead of the vertical direction as illustrated in FIG. 10. When the water filter is held in this orientation, the thickness of the water layer in the direction of the light path A—A can be adjusted by suitably changing the amount of water held in the cavity. In this case, it is desirable to keep a transparent lid 37 floating on the surface of the water layer to insure perfect planarity of the water surface.

In the first through third embodiments described above, for the adjustment of the intensity of the output light on the surface of the sample plane 17, there may be conceived various ideas such as:

(a) disposing a diaphragm or a mesh between the light sources (incandescent filament lamp 12 and xenon short arc lamp 11), and the sample plane 17, (b) moving the reflecting mirrors (focusing mirrors 15, 16) for the light sources toward or away from the light sources, and (c) varying the excitation voltages or electric currents for the xenon short arc lamp 11 and the incandescent filament lamp 12.

These concepts, however, are suspected to entail the following drawbacks.

(A) When the diaphragm and the mesh are disposed as described above, they are deformed on exposure to heat. This deformation prevents the control of the amount of light from being carried out accurately and affects the parallelism of lights and the uniformity of the beam intensity on the sample plane 17.

(B) When the focusing mirrors disposed behind the light sources are moved toward or away from the light sources, the parallelism of lights and the illumination distribution are affected. Particularly, in the case of the xenon short arc lamp 11, the light emitted from the red-hot anode plate mingles into the output light and affects the spectral distribution and color temperature of the output light.

(C) When the excitation voltage or the electric current is varied, the spectral distribution of the light from the incandescent filament lamp (tungsten halogen lamp) is varied at the same time. Thus, the approximation of the spectral distribution of the synthetic output light to the spectral distribution of natural sunlight is impaired.

In the fourth and fifth embodiments of the present invention aimed at avoiding the drawbacks enumerated above and materializing effective control of the intensity of the output light, the intensity of light on the sample plane is adjusted, in the case of the incandescent filament lamp, by moving the lamp toward or away from the sample plane in the direction of the optical axis and, in the case of the xenon short arc lamp, by controlling the electric current supplied to the lamp and the position of the incandescent filament lamp and the magnitude of the electric current supplied to the xenon short arc lamp are synchronously adjusted so that when the intensity of light from one of the light sources on the sample plane is varied, the intensity of light from the other light source on the sample plane is proportionally varied and the difference or ratio between the intensities of lights from the two light sources equals the value fixed in advance in conformity with the intensity of the output light.

Figure 12:
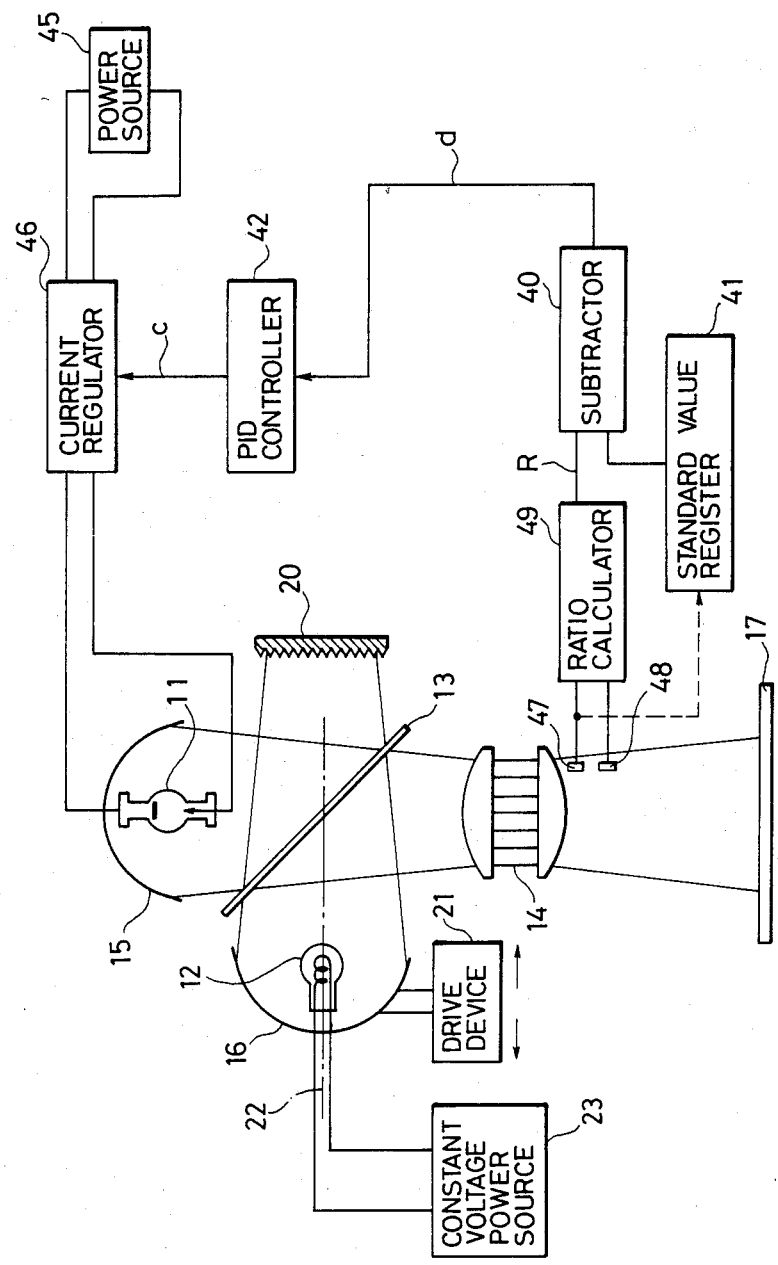
FIG. 12 is a schematic side view of the fourth embodiment of this invention and a block diagram of an electric control circuit.

FIG. 12 is a diagram illustrating in outline the construction of the fourth embodiment of the present invention. In this diagram, the same numerical symbols as used in FIG. 5 denote identical or equivalent components.

A constant voltage power source 23 serves to energize and turn on the incandescent filament lamp 12. A drive device 21 moves the incandescent filament lamp 12 and the focusing mirror 16 as a unit in the direction of the optical axis 22. Of the light emitted by the incandescent filament lamp 12, the portion of the near infrared component extracted by the filter means 13 which impinges on the integrating optical system 14 increases or decreases, with the result that the intensity (or amount) of the light from the incandescent filament lamp 12 which reaches the sample plane 17 is proportionately varied.

A power source 45 supplies a prescribed electric current to the xenon short arc lamp 11 through a current regulator 46 and causes the xenon short arc lamp 11 to discharge.

A photoelectric transducer 47 for the incandescent filament lamp serves to measure the intensity of the light emitted by the incandescent filament lamp 12. This photoelectric transducer 47 is combined with a band pass filter adapted to permit passage of light in the range of 900 to 1,000 nm, for example.

A photoelectric transducer 48 for the xenon lamp serves to measure the intensity of the light emitted by the xenon short arc lamp 11. This photoelectric transducer is combined with a band pass filter adapted to pass the light in the range of 400 to 500 nm.

Evidently, the aforementioned ranges of wavelength are freely selectable on the basis that the range of wavelength to be selected for one light source should not be affected by variation in the light emitted from the other light source.

A ratio calculator 49 is supplied with two outputs from the aforementioned photoelectric transducers 47 and 48, and calculates the ratio R between the two outputs.

A subtractor 40 compares the ratio R with the standard value (or target value) set in advance in a standard value register 41 and calculates the deviation d of the aforementioned ratio from the aforementioned standard value.

A PID controller 42 performs a proper arithmetic operation (such as, for example, proportionation, integration and differentiation) based on the aforementioned deviation d and provides a control command C.

The aforementioned control command C is supplied to a current controller 46, to control the magnitude of electric current supplied to the xenon short arc lamp 11 so as to null the aforementioned deviation d.

As easily understood by any person of ordinary skill in the art, the current controller 46, the photoelectric transducers 47 and 48, the ratio calculator 49, the subtractor 40, the standard value register 41, and the PID controller 42 from a feedback control loop. Evidently, the control loop is not limited to the illustrated configuration but may be suitably selected.

During the operation of the solar simulator, the incandescent filament lamp 12 is lit up by the constant voltage power source 23 and the xenon short arc lamp 11 is lit up by the power source and the current controller 46. In this case, the electric current supplied to the xenon short arc lamp 11, as evident from the description given afterward, is controlled to a fixed level so that the intensity (or amount) of the light emitted thereby will equal the value set in advance.

Figure 4:
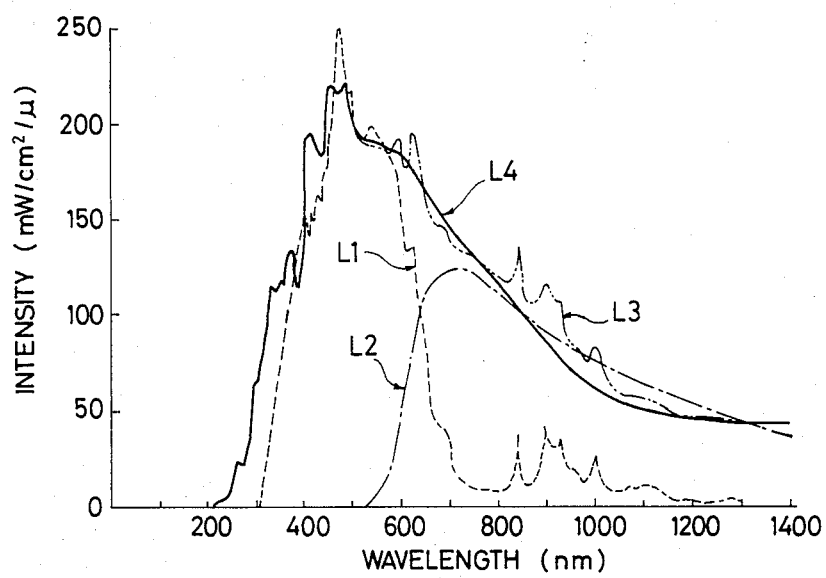
FIG. 4 is a diagram illustrating the spectral distribution characteristic of a synthetic light obtained by overlapping a xenon short arc lamp and an incandescent filament lamp and that of natural sunlight.

As the result, a simulated sunlight possessing a spectral distribution as indicated by the curve L3 in FIG. 4, for example, which closely approximates the spectral distribution of natural sunlight is projected on the sample plane 17.

For a desired variation in the intensity (or illumination) of light on the sample plane 17, the incandescent filament lamp 12 and the focusing mirror 16 are firstly moved as a unit by the drive device 21 toward or away from the integrating optical system on the optical axis 22 (toward the left or right in the arrangement of FIG. 12).

Figure 1:
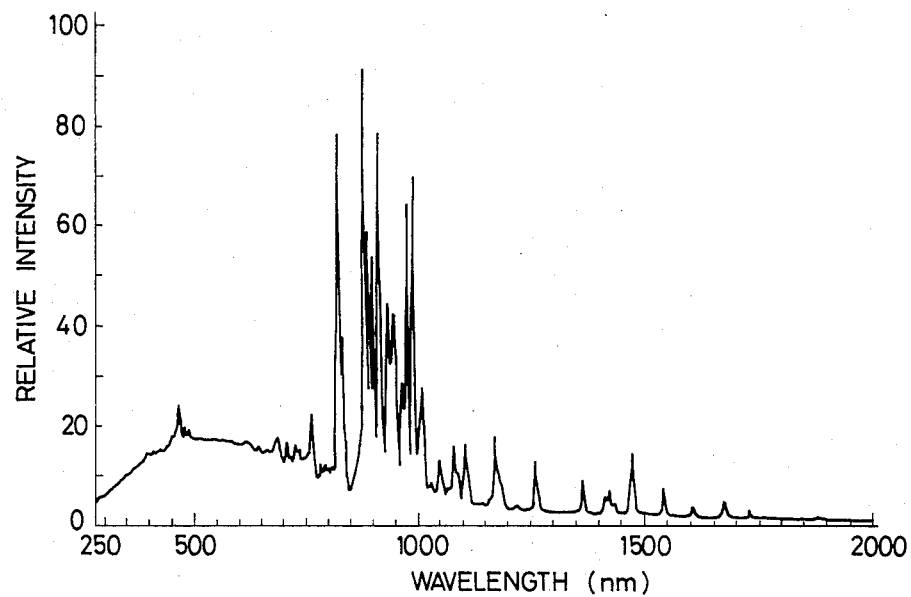
FIG. 1 is a diagram illustrating a spectral distribution of a light emitted by a xenon short arc lamp.
Figure 2:
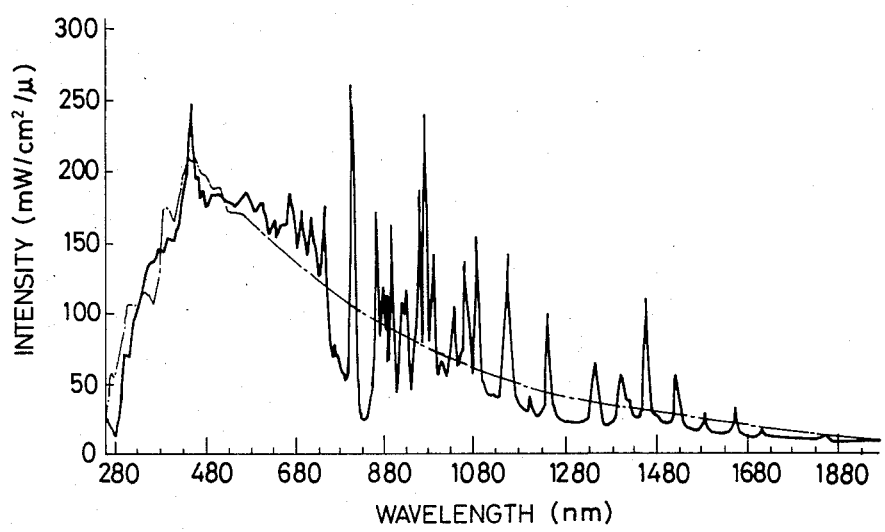
FIG. 2 is a diagram illustrating a compensated spectral distribution of the light from the xenon short arc lamp as compared with the spectral distribution of natural sunlight.

If the incandescent filament lamp 12 and the focusing mirror 16 are moved forwardly (toward the right in FIG. 1), for example, of the light emitted by the incandescent filament lamp 12, the near infrared component extracted by the aforementioned filter means and caused to impinge on the integrating optical system 14 grows in amount. As the result, the intensity of the light of the incandescent filament lamp 12 on the sample plane 17 becomes large as indicated by the curve L2A in FIG. 13.

To obtain projection of light possessing a spectral distribution approximating that of natural sunlight on the sample plane 17, it becomes necessary for the light emitted by the xenon short arc lamp 11 to be increased proportionately to the aforementioned increase of the light from the halogen or incandescent lamp.

In the present embodiment, therefore, photoelectric transducers 47, 48 for the incandescent filament lamp and the xenon lamp are disposed respectively in the paths for the lights of the incandescent filament lamp 12 and the xenon short arc lamp 11 (specifically between the integrating optical system 14 and the sample plane 17) to measure intensities (amounts) of the lights issuing from the xenon short arc lamp 11 and the incandescent filament 12 and reaching the sample plane 17 independently of each other.

The signals representing the intensities so measured are supplied to the ratio calculator 49, which determines the ratio R by calculation. In the subtractor 40, this ratio R is compared with the standard value of ratio set in the standard value register 41 to calculate the deviation d.

Then, by the feedback control known to the art, a proper signal required to null the aforementioned deviation d is delivered to the current controller 46, to effect necessary control of the energizing current supplied to the xenon short arc lamp 11.

In the manner described above, the ratio between the intensities of lights radiating from the xenon short arc lamp 11 and the incandescent filament lamp 12 and reaching the sample plane 17 is retained at the prescribed level.

Figure 13:
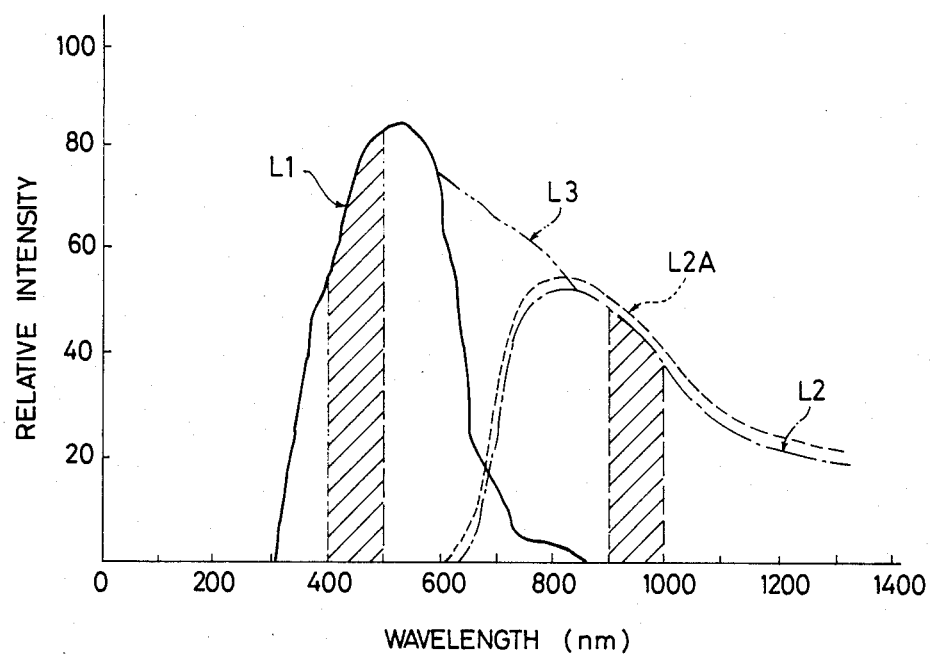
FIG. 13 is a spectral diagram for illustration of the operation of the aforementioned fourth embodiment.

As is seen from FIG. 13 or FIG. 4, therefore, the synthetic spectral distribution on the sample plane 17 is kept substantially at the target value.

In the fourth embodiment of FIG. 12, the amount of the light radiating from the incandescent filament lamp 12 and reaching the sample plane 17 is first varied and then the amount of the light from the xenon short arc lamp 11 is controlled proportionately to the variation so as to produce a desired spectral distribution. Apparently this procedure may be reversed, i.e. the amount of the light radiating from the xenon short arc lamp 11 and reaching the sample plane 17 is first varied and the amount of the light from the incandescent filament lamp 12 is then controlled proportionately to the variation so as to obtain the spectral distribution.

Figure 14:
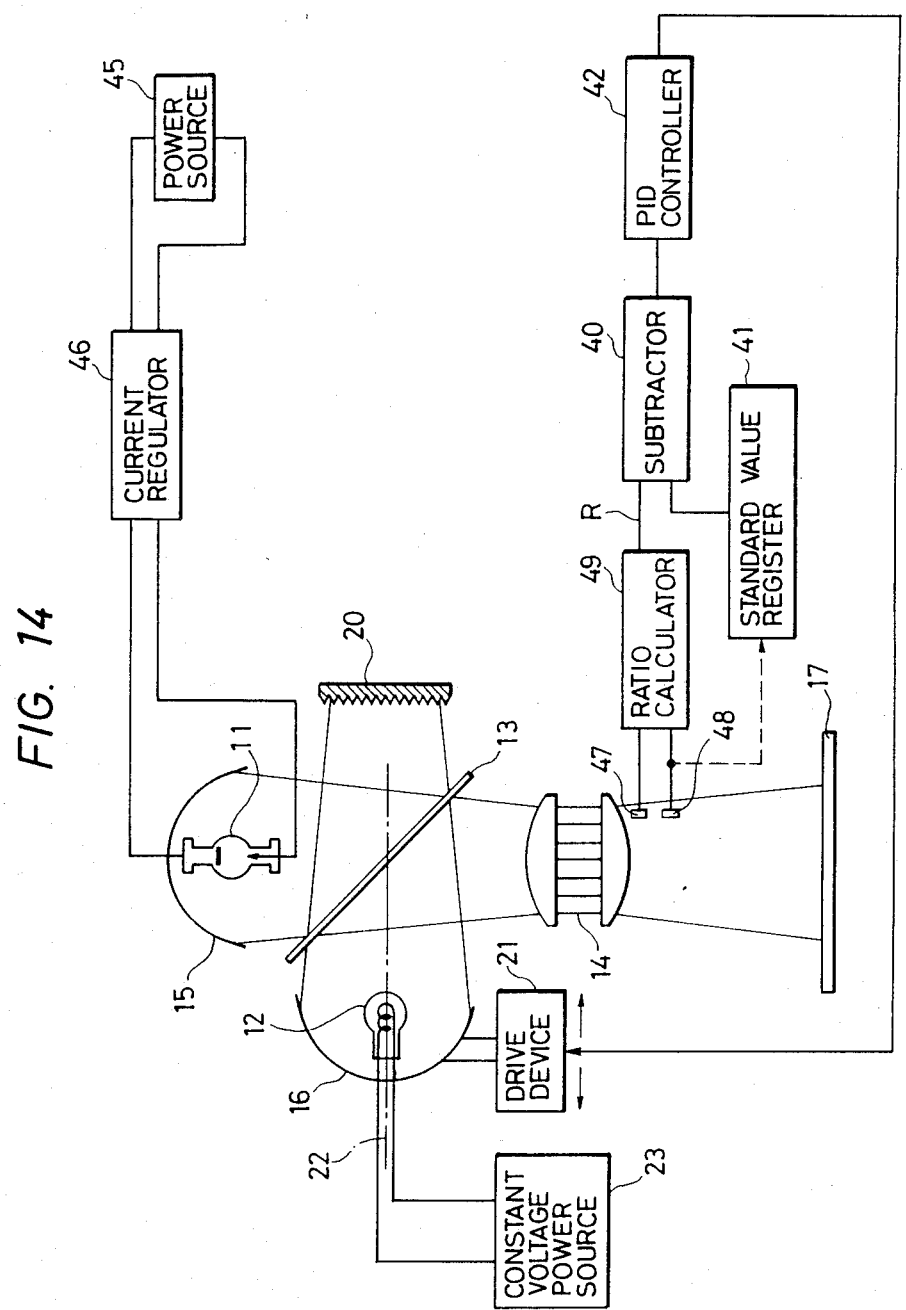
FIG. 14 is a schematic side view of the fifth embodiment of this invention and a block diagram of an electric control circuit.

FIG. 14 is a diagram illustrating in outline the construction of the fifth embodiment of this invention aimed at effecting the control mentioned above. In this diagram, the same numerical symbols as found in FIG. 12 denote identical or equivalent components.

As noted clearly from the comparison of FIG. 14 with FIG. 12, the fifth embodiment equals the fourth embodiment, except that the spectral distribution on the sample plane 17 is controlled as desired by controlling the drive device 21 with the control output of the PID calculator 42 and consequently controlling the positions of the incandescent filament lamp 12 and the focusing mirror 16 on the optical axis 22.

The operation of the embodiment of FIG. 14 is apparent to any person of ordinary skill in the art so no further explanation is needed.

This invention can be modified as follows.

(1) The spectral distribution can be obtained substantially as desired on the sample plane 17 by substituting a subtractor for the ratio calculator 49 and using the difference between the two outputs of the transducers in the place of the ratio R therebetween as an input for the subtractor 40.

(2) At least either of the photoelectric transducer 47 for the incandescent lamp and the photoelectric transducer 48 for the xenon lamp is disposed between the corresponding light source and the heat reflecting cold filter 13.

(3) The heat transmitting cold mirror 19 is used as illustrated in FIG. 6 in the place of the heat reflecting cold filter 13 illustrated in FIG. 12 or FIG. 14 and the xenon short arc lamp 11 and the incandescent filament lamp 12 are disposed as illustrated in FIG. 6. In any other respect, the construction is similar to that of FIG. 12 or FIG. 14.

(4) The standard value register 41 is adapted so that the value set therein will be varied as indicated by the dotted line with a prescribed relation, depending on the output of the photoelectric transducer 47 for the incandescent lamp in FIG. 12 or the output of the photoelectric transducer 48 for the xenon lamp in FIG. 14, respectively. In this arrangement, the light of the various spectral distribution and intensity conforming with amount of cloud or air mass can be reproduced on the sample plane 17.

(5) The photoelectric transducer 47 for the incandescent lamp and the photoelectric transducer 48 for the xenon lamp can be substituted with some other suitable means capable of measuring light intensity.

(6) The feedback control is substituted with an open loop control. For example, the amount of light from one of the two light sources 11 and 12 is measured and either of the current controller 46 and the drive device 21 which controls the amount of the light from the other light source, is adjusted so as to cause the other light source to radiate an amount of light which depends on the value obtained by the measurement.

EFFECT OF THE INVENTION

As noted from the foregoing description, this invention brings about the following effects:

(1) Since the number of filters required for the operation can be halved, the apparatus can be decreased in size and the cost lowered.

(2) Since one common filter can effect both the elimination of near infrared component from the light emitted by the xenon short arc lamp and the extraction of the near infrared component from the light emitted by the incandescent filament lamp, the synthetic spectral distribution characteristic is improved in uniformity and repeatability.

(3) The synthetic spectral distribution can be approximated more closely to the spectral distribution of natural sunlight.

(4) The intensity of light emitted by the solar simulator can be easily and extensively varied without jeopardizing the spectral distribution, parallelism, and even illumination of the output lights.

What is claimed is:

1. A solar simulator, comprising
   a xenon short arc lamp,
   an incandescent filament lamp,
   filter means capable of eliminating a near infrared component from the light emitted by said xenon short arc lamp and, at the same time, extracting a near infrared component from the light emitted by said incandescent filament lamp, and
   a single integrating optical system on which the light emitted by said xenon short arc lamp minus said near infrared component and the light of said near infrared component extracted by said filter means from the light emitted by said incandescent filament lamp impinge.

2. A solar simulator according to claim 1, wherein said filter means is a cold filter disposed diagonally relative to an optical axis of said integrating optical system and adapted to reflect the near infrared component of light, and said xenon short arc lamp is disposed on the optical axis of said integrating optical system and behind said cold filter, and said incandescent filament lamp is disposed in front of said cold filter.

3. A solar simulator according to claim 1, wherein said filter means is a heat transmitting cold mirror disposed diagonally relative to an optical axis of said integrating optical system and adapted to permit passage of the near infrared component, and said incandescent filament lamp is disposed on the optical axis of said integrating optical system and behind said heat transmitting cold mirror, and said xenon short arc lamp is disposed in front of said cold mirror.

4. A solar simulator according to claim 1, wherein an infrared spectrum compensating means capable of weakening the infrared component of the spectrum of the light emitted by said incandescent filament lamp and elevating the color temperature thereof is disposed on the optical path leading from said incandescent filament lamp to said filter means.

5. A solar simulator according to claim 4, wherein said infrared spectrum compensating means is a multilayer reflection surface permitting partial passage of infrared light.

6. A solar simulator according to claim 1, wherein said filter means is a multilayer interference filter.

7. A solar simulator according to claim 1, which further comprises a water filter disposed in the path of the light emitted by said incandescent filament lamp.

8. A solar simulator according to claim 7, wherein said water filter is disposed so that the water surface lies horizontally and the optical axis intersects substantially vertically said water surface.

9. A solar simulator provided with a xenon short arc lamp, an incandescent filament lamp, filter means capable of eliminating a near infrared component from the light emitted by said xenon short arc lamp and, at the same time, extracting a near infrared component from the light emitted by said incandescent filament lamp, and a single integrating optical system on which the light emitted by said xenon short arc lamp minus said near infrared component and the light of said near infrared component extracted by said filter means from the light emitted by said incandescent filament lamp impinge, which solar simulator further comprises

- drive means for moving said incandescent filament lamp toward or away from a sample plane along the optical axis thereof,
- means for controlling electric current supplied to said xenon short arc lamp,
- a constant voltage power source for energizing said incandescent filament lamp,
- means for measuring the intensity of light from said xenon short arc lamp and the intensity of light from said incandescent filament lamp,
- means for comparing said measured intensities of light from said xenon short arc lamp and said incandescent filament lamp respectively, and providing an output representing a function of the comparison,
- means for calculating deviation of the output of said comparison means from a standard value, and
- means for selectively controlling at least one of said drive means for said incandescent filament lamp and said current control means for said xenon short arc lamp as a function of said deviation to null said deviation.

10. A solar simulator according to claim 9, wherein said means for measuring the intensity of light from said incandescent filament lamp is a band pass filter having a transmission band width in a region having a longer wavelength than 750 nm.

11. A solar simulator according to claim 9, wherein said means for measuring the intensity of light from said xenon short arc lamp is a band pass filter having a transmission band width of shorter wavelength than 750 nm.

12. A solar simulator according to claim 9, wherein each of said means for measuring the intensity of light from said xenon short arc lamp and said incandescent filament lamp is disposed opposite the respective light source relative to said integrating optical system.

13. A solar simulator according to claim 9, wherein said standard value is set as a function of the intensity of light from said incandescent filament lamp.

14. A solar simulator according to claim 9, wherein said means for comparing the intensities of light comprises the calculation of the ratio between said intensities.

15. A solar simulator according to claim 9, wherein said means for comparing the intensities of light comprises the calculation of the difference between the said intensities.

* * * * *